(12) United States Patent
Schmalberger et al.

(10) Patent No.: US 6,491,640 B1
(45) Date of Patent: Dec. 10, 2002

(54) INJECTION CHANNEL FOR A BLOOD VESSEL CATHETER

(75) Inventors: Rainer Schmalberger, Munich (DE); Matthias Fahle, Munich (DE); Ulf Borg, Munich (DE); Ulrich Pfeiffer, Munich (DE)

(73) Assignee: Pulsion Medical Systems AG, Munich (DE)

( * ) Notice: Subject to any disclaimer, the term of this patent is extended or adjusted under 35 U.S.C. 154(b) by 0 days.

(21) Appl. No.: 09/515,218

(22) Filed: Feb. 29, 2000

(30) Foreign Application Priority Data

Mar. 6, 1999 (EP) .............................................. 99104535

(51) Int. Cl.[7] ................................................. A61B 5/02
(52) U.S. Cl. ........................................ 600/526; 600/504
(58) Field of Search ................................. 600/507, 526, 600/504, 505; 604/246–247, 113–114; 222/638, 639; 968/833, 836

(56) References Cited

U.S. PATENT DOCUMENTS 4,213,021 A * 7/1980 Alexander
4,730,623 A    3/1988 Lee
5,009,234 A    4/1991 Alt
5,595,181 A    1/1997 Hubbard
5,713,864 A *  2/1998 Verkaart
6,290,681 B1 * 9/2001 Brown

FOREIGN PATENT DOCUMENTS

EP          0 900 545         3/1999

* cited by examiner

*Primary Examiner*—Mark Bockelman
(74) *Attorney, Agent, or Firm*—Squire, Sanders & Dempsey, L.L.P.

(57) ABSTRACT

The present invention is directed to an apparatus and method for injecting an injectate fluid into a blood vessel of a patient for carrying out thermodilution or dye-dilution measurements in order to determine hemodynamic parameters of the patient. The apparatus includes sensing means for sensing a change of pressure and/or flow rate and/or temperature inside the injection channel, and a computer coupled to the sensing means for determining the time instants of start and finish of the injection process.

23 Claims, 5 Drawing Sheets

INJECTION CHANNEL FOR A BLOOD VESSEL CATHETER

BACKGROUND OF THE INVENTION

1. Field of Invention

The invention is a device to detect the start and end of injection as well as the injectate temperature during thermodilution determination of cardiocirculatory parameters and intra- and extravascular volumes.

2. Description of Related Arts

Cardiac Output (CO) and circulating blood volume are very important parameters to diagnose the condition of clinically ill patients. Measuring these parameters is a very important part of intensive care as well as in medical research. Such measurements are typically performed on critically ill patients in head surgical treatment and for pharmacological management strategies.

When employing a method of thermodilution for cardiac output determination, a liquid indicator colder than the blood temperature is injected into the right atrium or the superior or inferior vena cava. After a period of time, depending on the blood flow through the head and pulmonary circulation, a temperature drop can be detected in the femoral artery. By plotting the temperature drop over time, the area under the resulting curve can be used to determine cardiac output. To calculate cardiac output, it is crucial to know the exact temperature of the blood and the injected liquid. The blood temperature can be measured with an indwelling thermistor in the femoral artery, using a sensor that can be a temperature dependent resistor with a negative coefficient (NTC).

The temperature of the injected liquid is also measured with a resistor of the same type. This resistor is in thermal contact with the liquid within the injection channel. Hence, the temperature of the injected liquid can be measured during injection. In order to reuse the sensor, a thermal bridge is established between the sensor and the fluid path using a liquid impermeable material. This device is called IITS device (IITS) and is a sterile disposable item. The IITS is connected in series with the injection channel and contains the holder for the temperature sensor. Additionally, in this device includes a membrane as an actuator of a timing device. The defined time intervals on the indicator dilution curve allow calculation of intra- and extravascular volumes between site of injection and site of detection. However, precise detection of the start and finish of the injection is necessary.

Since determining these specific time points manually is impractical and imprecise, detection of a sudden step function of the temperature in the IITS is used. A sudden change in temperature is achieved by using cold injectate through the IITS that is at room temperature before injection. Consequently the injectate must be cooled prior to injection. This necessary step is a big disadvantage to the user in the intensive care unit, operating room or ambulance, where time may be a critical factor. Furthermore, providing cold injectate imposes not only additional labor time but may also introduce measurement errors and health risk to the patient. If the injectate is removed from the cooling compartment and injection is delayed, the liquid may warm up and may result in erroneous measurement. Additionally, if several consecutive determinations are performed, the IITS will cool and temperature detection will deteriorate.

The use of conventional cooling set at the bedside does not adequately address the above mentioned problems. The cooling set can only provide cold injectate provided that ice is constantly replenished in the cooler. The additional cooler also represents an added expense.

SUMMARY OF THE INVENTION

Because of the disadvantages mentioned above, the ability to use injectate at room temperature would simplify the measurement. Preferred embodiments of the present invention is a device that allows detection of the injectate temperature as well as beginning and end of injection at room temperature. More specifically, preferred embodiments of the present invention allows a user to detect the start and finish of injection for a thermodilution measurement at room temperature (approximately 20 degrees Celsius) without using cooled or heated injectate.

DETAILED DESCRIPTION OF THE INVENTION

Figure 1:
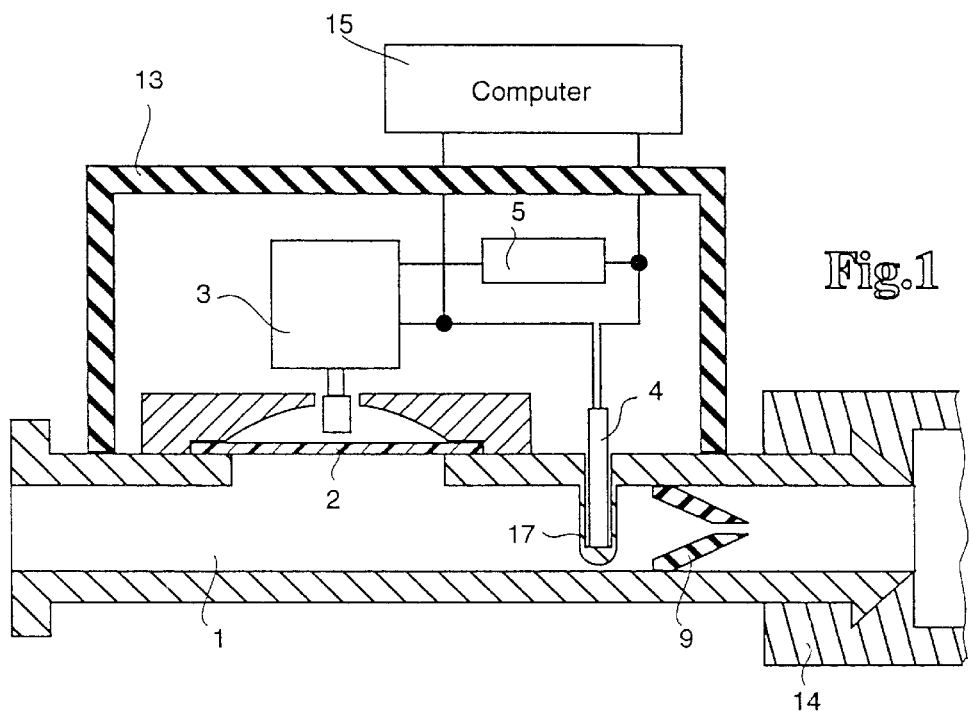
FIG. 1 is a cross sectional view of a preferred embodiment of the present invention.

FIGS. 1 illustrates a preferred embodiment of the present invention using a temperature depending resistor to measure the temperature of the injectate for a thermodilution measurement. The temperature depending resistor 4 may preferably be a PTC (positive coefficient of temperature) or a NTC (negative coefficient of temperature). Start and finish of injection is detected as step function of the resistance of the sensor branch for temperature measurement. The switch 3 and a resistor 5 can be connected parallel to the temperature depending resistor (temperature sensor 4) as shown in embodiments of FIGS. 1, 2, and 4 or in serial connection as shown in another embodiment of FIG. 3 to generate this step function. At the moment of injection, the switch 3 opens or closes and generates a sudden change of resistance of the overall set-up. Before the start of injection, a deviating value of the temperature is displayed, whereby at injection the true value is displayed.

A preferred embodiment of the present invention may employ an impedance in the channel of injection to cause a rise of pressure at injection. This resistance is the valve 9 in FIG. 1. It is set-up as a check valve and prevents back flow of liquid against the mainstream (no pressure rise at injection from the catheter side). Catheters with large cross sections are preferably used in the valve to assure that the pressure rise is still sufficient to displace the membrane 2. This membrane 2 is displaced and actuates the switch 3. The switch 3, depending on set-up, may close or open. Therefore, from the view of the acquisition computer, the overall resistance of the whole set-up including the thermistor 4 changes. At end of injection the switch 3 is reset due to the restoring force of the membrane 2.

Valve 9 and membrane are preferably dimensioned so that the valve 9 only opens when the pressure rise at injection is sufficient to displace the membrane 2 and actuate the switch 3. Switch, resistor and thermistor are preferably located in a common housing 13 that is removable. The same unit may be used in FIG. 2 where the housing is shown separated from the injection channel.

Figure 2:
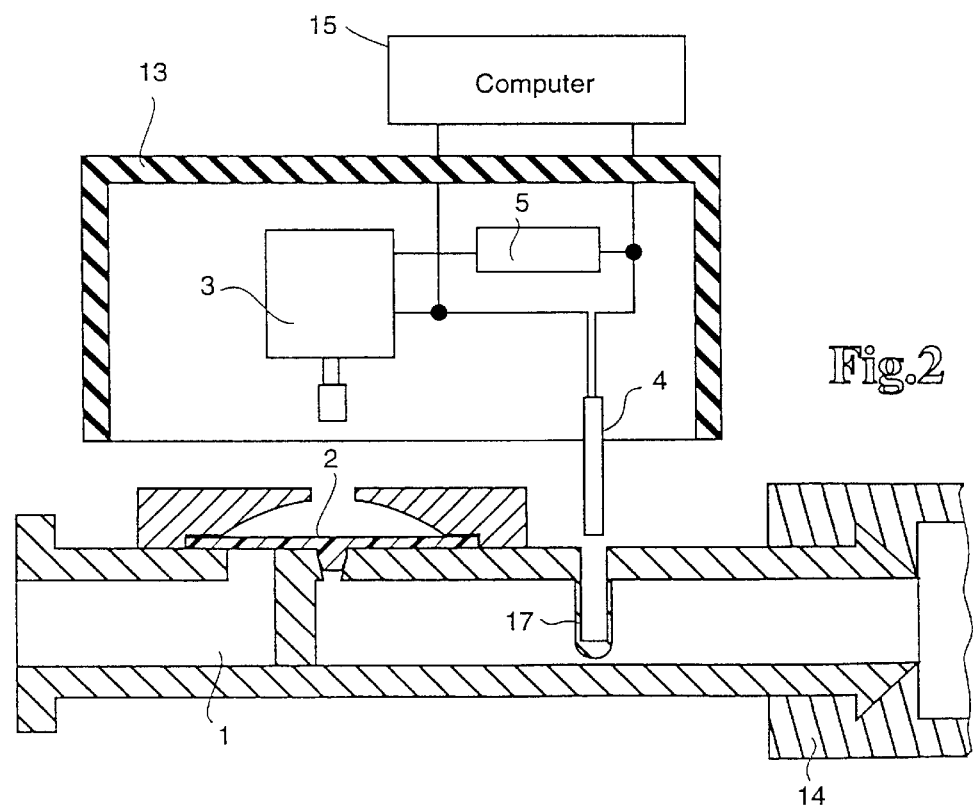
FIG. 2 is a cross sectional view of another preferred embodiment of the present invention.

FIG. 2 illustrates another embodiment of the present invention, which includes an Inline Injectate Temperature Sensor with a membrane 2, a holder 17 for the sensor and a temperature sensor 4. In this embodiment the pressure rise is transformed to a mechanical displacement of the membrane 2 that is preferably attached to the housing. The membrane 2 actuates the switch 3. The membrane 2 preferably acts as a barrier between atmosphere and pressure. If the membrane 2 is displaced, switch 3 opens or closes. At injection from the catheter side, the pressure rise caused by the pin on the membrane 2 closing the passage to the output, displaces the membrane 2. This pin is the variable impedance in the injection channel, opening the passage for the liquid, dependent on pressure and hence flow rate. If the pressure is sufficient to displace the membrane the liquid can flow causing the pressure to fall, hence this feedback keeps the pressure constant. At end of injection the restoring force of the membrane puts the pin back in position and switch 3 is reset. In this set-up the length of the pin sets the displacement of the membrane. It should be long enough, so that before it opens the passage, the switch 3 should be actuated by the displacement of the membrane. The tension of the membrane sets the opening pressure. In this variation the passage and the pin on the membrane 2 constitute the check valve in the previous variation. Liquid from the syringe side sees a large effective area, compared to liquid from the catheter side which sees only a small effective area, hence a large pressure is required to displace the membrane. The output of the circuit is preferably a cable with two wires that are hooked up to a data acquisition device.

Figure 3:
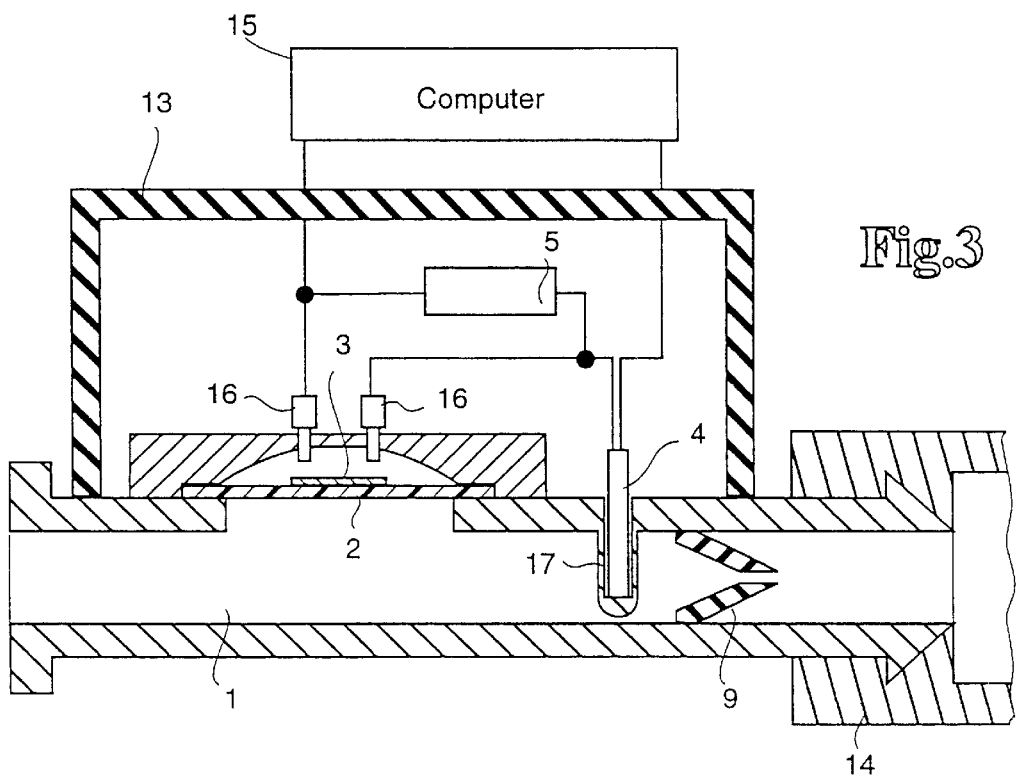
FIG. 3 is a cross sectional view of another preferred embodiment of the present invention.

Another embodiment of the present invention is shown in FIG. 3. In this embodiment the switch 3 is preferably not located in housing 13. Rather, the switch 3 is preferably integrated in the disposable Inline Injectate Temperature Sensor device. A conductive coating on the atmospheric side of the membrane 2 and two contacts molded into the support of the membrane constitute the switch 3 in this embodiment. Before injection, the switch 3 is preferably open. At injection the pressure in the IITS rises and displaces the membrane 2. This displacement makes the conductive coating of the membrane to touch the contacts and hence the switch 3 is closed. For function of this setup it is necessary to use the circuit in which the switch 3 is connected in series to the temperature sensor as shown in FIG. 3, since at injection the switch is closed and not opened. The other parts of the setup are the valve with the variable impedance 9, the contacts 16 on the removable housing 13, the holder 17 for the temperature sensor, the resistor 5 and the temperature sensor.

Figure 4:
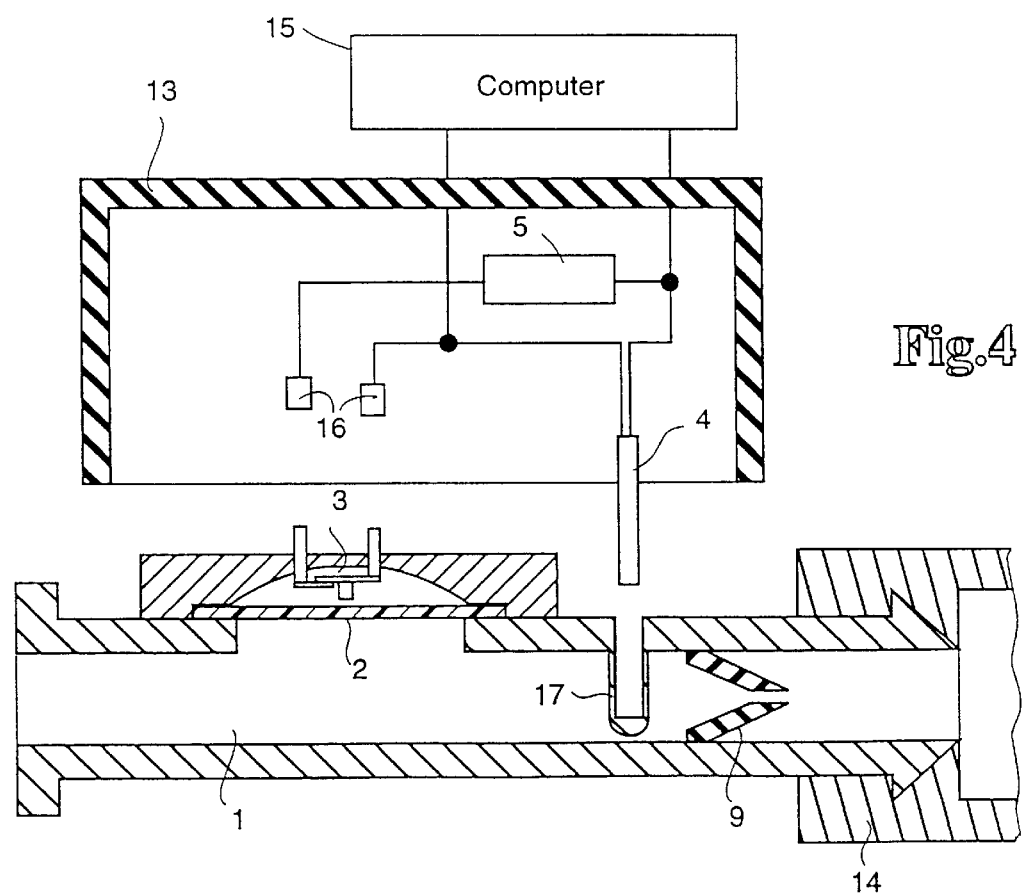
FIG. 4 is a cross sectional view of another preferred embodiment of the present invention.

Another embodiment of the present invention is shown in FIG. 4. The switch 3 is preferably integrated in the IITS. Before injection, the switch 3 is closed. When injection happens the membrane is displaced and switch 3 opens. Since this setup works with opening of the switch at injection a circuit must be used in which the switch is connected parallel to the temperature sensor as shown in FIG. 4.

Figure 5:
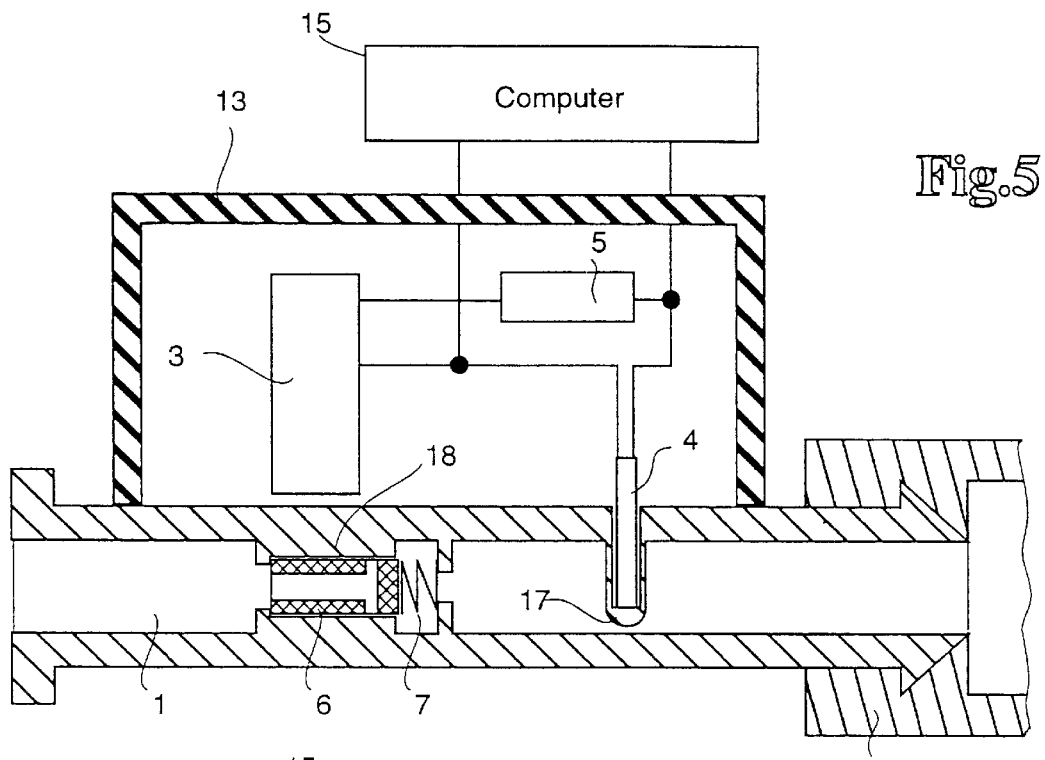
FIG. 5 is a cross sectional view of another preferred embodiment of the present invention.

FIG. 5 shows another embodiment of the present invention. A Reedswitch is preferably used as switch 3. In the injection channel there is a piston/magnet 6 made preferably from magnetic material. It has an axial blind hole and one or more radial holes. If the piston 6 is in the proximity of the Reedswitch 3, the magnet actuates the switch. If the piston 6 is distant from the Reedswitch 3 there is no influence from the magnetic field of the piston 6.

Spring 7 pushes piston 6 in the piston guide 18. In the resting position the radial holes are preferably closed and prevent any flow of liquid. Injection causes a pressure rise which moves the piston 6 against the restoring force of the spring 7 out of the piston guide 18. If the radial holes protrude from the piston guide liquid can flow and the pressure will not continue to rise. The displacement of the piston 6 preferably prevents the magnetic field from influencing the Reedswitch 3 and the switch 3 opens or closes. When pressure falls at end of injection, piston 6 is preferably forced back into the piston guide by spring 7 and the Reedswitch is reset. The change of the overall resistance of the setup is achieved by combination of Reedswitch 3 with resistor 5 and temperature sensor 4 in a common removable housing.

Figure 6:
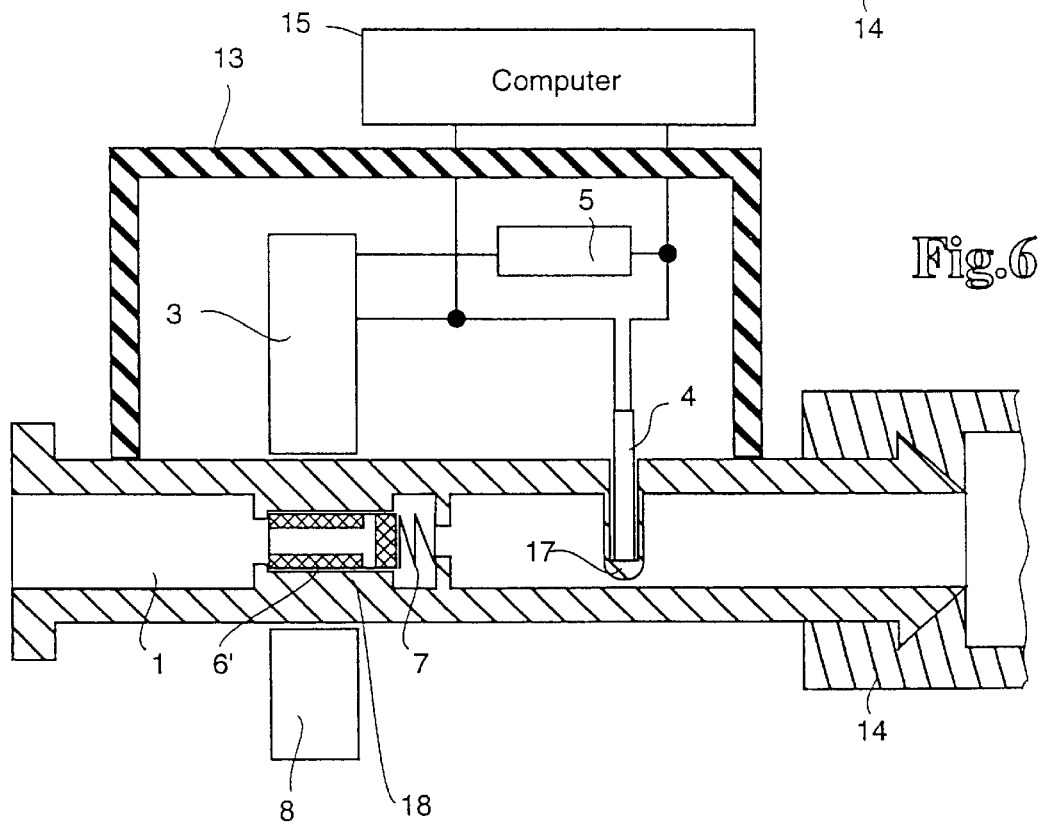
FIG. 6 is a cross sectional view of another preferred embodiment of the present invention.

Another embodiment of the present invention is shown in FIG. 6. A Reedswitch 3 is preferably used. In the injection channel there is piston 6 made preferably from ferromagnetic metal. It has a blind hole and one or more radial bore. In the piston between magnet 8 and Reedswitch 3 the metal deflects the magnetic field from the Reedswitch 3. If the piston is not present, the magnetic field can actuate the Reedswitch. Spring 7 pushes piston 3 in the piston guide 18. In the resting position the radial holes are obstructed by the piston guide and no liquid can flow. At injection the pressure rise moves the piston 6 against the restoring force of the spring 7 out of the piston guide. Liquid flows when the radial holes in the piston protrude out of the piston guide 18. The displacement of the metal allows the magnet to open or close the Reedswitch. At end of injection the piston is pushed back in its original position by the spring 7 and the Reedswitch is reset. The change in resistance at injection is attained with the combination of Reedswitch 3 with resistor 5 and temperature sensor 4, which are in a common removable housing 13. Index 17 labels the holder for the temperature sensor 4.

Figure 7:
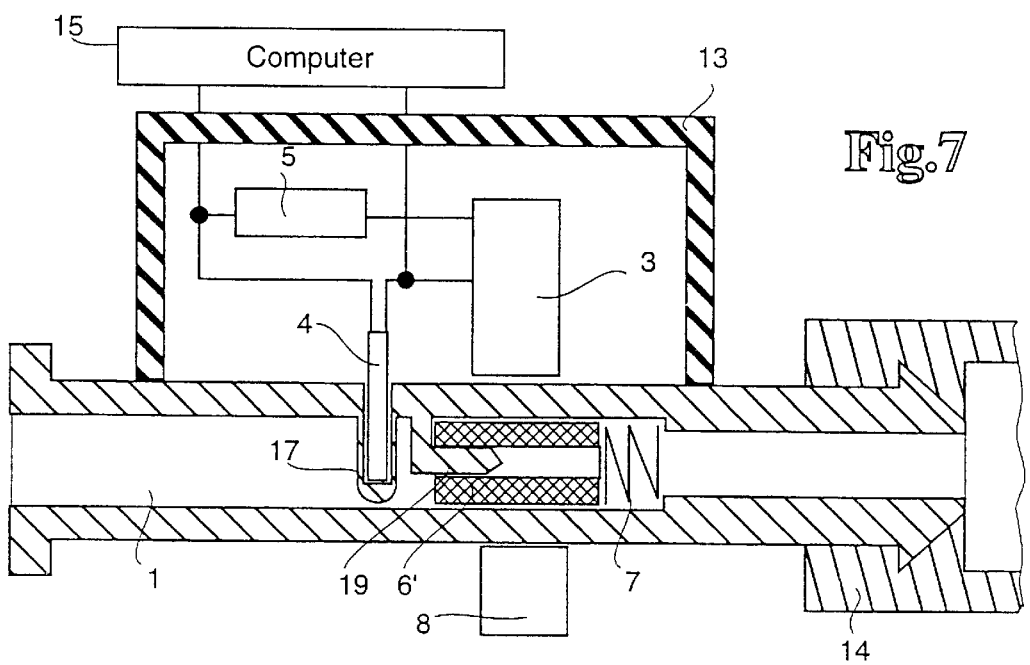
FIG. 7 is a cross sectional view of another preferred embodiment of the present invention.

A ferromagnetic metal is used in another embodiment of the present invention as shown in FIG. 7. A Reedswitch 3 is preferably used. In the injection channel there is piston 6' made from ferromagnetic metal, which may be closed by pin 19. In the piston between magnet 8 and Reedswitch, the metal preferably deflects the magnetic field from the Reedswitch 3. If the piston 6' is not present, the magnetic field can actuate the Reedswitch 3. Spring 7 pushes piston 6' towards the plug 19. In the resting position the bore of the tube is obstructed by the plug and no liquid can flow. At injection the pressure rise moves the piston 6' against the restoring force of the spring 7 out of the plug 19. Liquid flows when the plug 19 no longer closes the bore. The displacement of the metal allows the magnet to open or close the Reedswitch 3. At end of injection the piston 6' is preferably pushed back in its original position by the spring 7 and the Reedswitch 3 is preferably reset. The change in resistance at injection is attained with the combination of Reedswitch 3 with resistor 5 and temperature sensor 4, which are in a common housing 13. Index 17 labels the holder for the temperature sensor 4.

Figure 8:
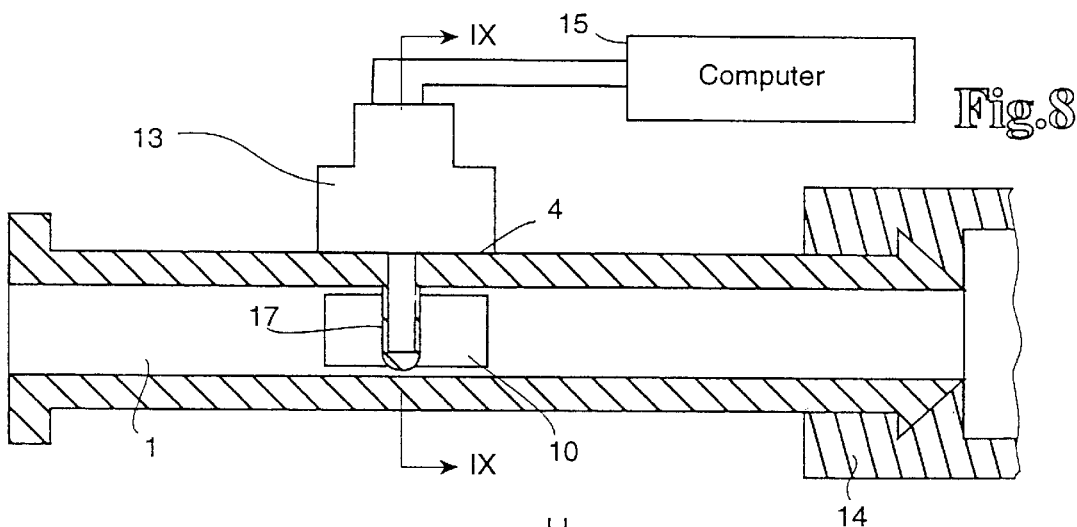
FIG. 8 is a cross sectional view of another preferred embodiment of the present invention.
Figure 9:
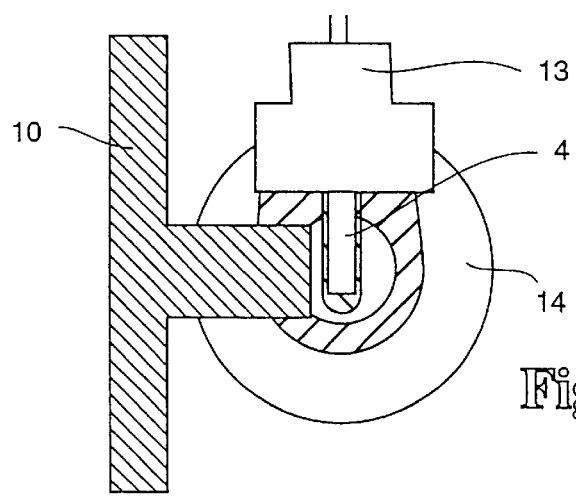
FIG. 9 is a top view of a preferred embodiment of the present invention.

If the IITS device is at body temperature (see also FIG. 8), there is no need to cool the injectate. The liquid inside the Inline Injectate Temperature Sensor, with the holder 17 for the temperature sensor 4, is warmed up via the Heat Contact Plate 10 made from nonsensitizing, heat conducting material that is applied to the skin of the patient. The increase in temperature depends upon the temperature of the skin, the location and on the ambient conditions. However, most of the time it is significantly higher than the room temperature (on average differs more than 2° C.). The small volume of liquid in the IITS is warmed up via the heat bridge 10 which is in thermal contact to the Heat Contact Plate, to a temperature that is higher than the room temperature. At injection the injectate at room temperature causes a sudden change in temperature that can be detected by the data acquisition system. After injection the liquid in the Inline Injectate Temperature Sensor is once again heated up by the body heat of the patient, and the end of the injection can be detected.

Figure 10:
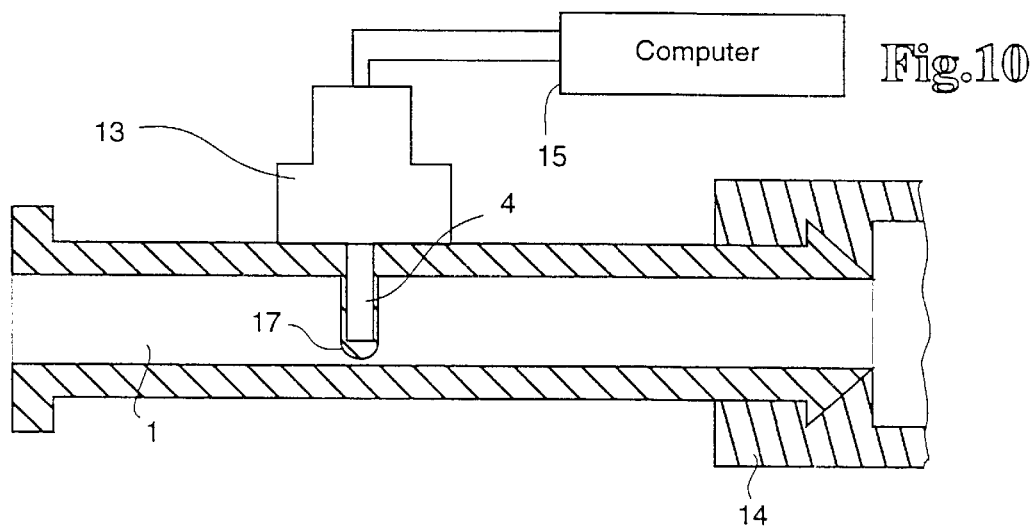
FIG. 10 is a cross sectional view of another preferred embodiment of the present invention.

In FIG. 10, the temperature difference prior to injection of injectate at room temperature is produced with the help of external energy supplied by the data acquisition computer 15. The temperature sensor 4 is preferably located in a holder 17 in the IITS and operated with high and constant measurement current. The high current heats up the thermistor 4, which dissipates the heat to its surroundings, the holder and hence the static liquid the holder 17. The power supplied to the thermistor 4 is preferably kept constant. The power supplied is preferably sufficient to cause a difference in temperature of 2° C. for the static compared to the dynamic one. The measured difference in temperature is preferably created by the gradient of temperature of heat transfer. This gradient is different for the static and the dynamic case. The measured temperature is the real temperature of the injectate plus an offset due to the heating of the thermistor, which has to be accounted for. This offset also changes with the liquid used and the difference of the injectate temperature from the room temperature. At the end of injection, when there is now flow of liquid and the static case is present, the measured temperature due to the self heating of the thermistor rises and the end of injection can be detected.

Figure 11:
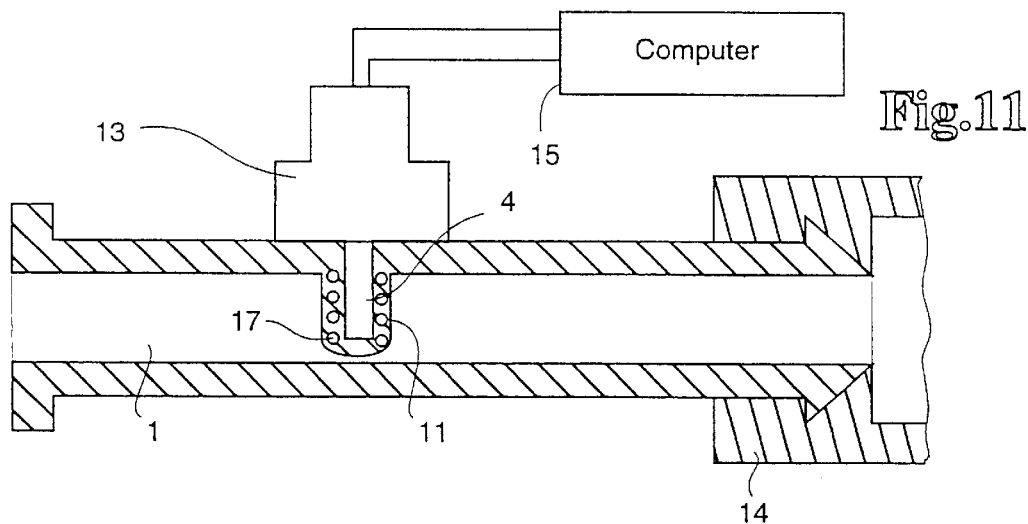
FIG. 11 is a cross sectional view of another preferred embodiment of the present invention.

In FIG. 11, the difference in temperature is produced with an external heater that is supplied from a battery or the data acquisition computer 15.

Figure 12:
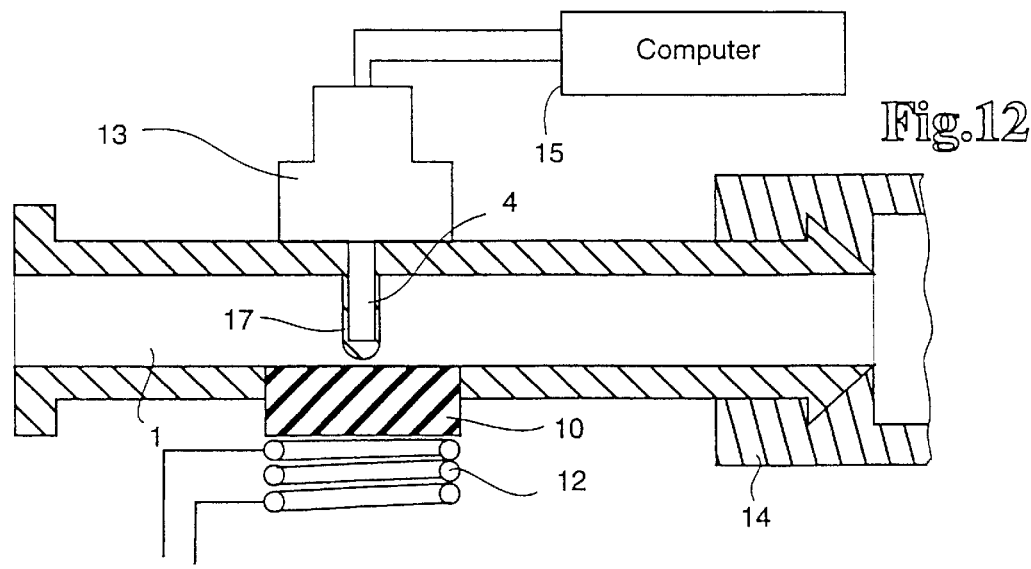
FIG. 12 is a cross sectional view of another preferred embodiment of the present invention.

In FIG. 12, the liquid in the Inline Injectate Temperature Sensor is heated by electrical means. The necessary energy is supplied by the data acquisition computer 15 or an external source like a battery. The electrical heating 12 is attached to the IITS. It is in thermal contact with the Heat Contact Plate 10 of the IITS. Since the small amount of liquid in the Inline Injectate Temperature Sensor is heated, injectate at room temperature generates a sudden change in temperature at injection. After injection the liquid remaining in the Inline Injectate Temperature Sensor is heated again, causing a rise in temperature, which signals the end of the injection. This method requires relatively more power to heat up the liquid within a given time, since more heat is transferred to its surroundings.

What we claim:

1. An injection channel for a blood vessel catheter for injecting an injectate fluid into a blood vessel of a patient for carrying out thermodilution or dye-dilution measurements in order to determine hemodynamic parameters of the patient, the injection channel comprising:

a temperature sensor inside the injection channel for sensing the temperature of the injectate fluid passing through the injection channel;

a computer coupled to the temperature sensor for detecting changes of temperature readings as instants of begin and end of an injection process; and a flow rate switch which is opened or closed if the flow rate in the injection channel exceeds a threshold, wherein the flow rate switch is electrically coupled to the output of the temperature sensor in such a manner that in case the flow rate inside the injection channel is lower than the threshold, the readings of the temperature sensor are modified to indicate a temperature which deviates from the true temperature readings and in case the flow rate inside the injection channel is exceeding the threshold, the readings of the temperature sensor are switched abruptly to the true readings.

2. The injection channel according to claim 1, wherein the flow rate switch is coupled to the computer which detects the actuation of the flow rate switch as instants of begin and end of the injection process.

3. The injection channel according to claim 1, wherein the flow rate switch is an NO-switch and is coupled in a serial circuit with regard to the output of the temperature sensor.

4. The injection channel according to claim 1, wherein the flow rate switch is an NC-switch and is coupled in a parallel circuit with regard to the output of the temperature sensor.

5. The injection channel according to claim 1, wherein a resistor is coupled in series to the temperature sensor and the flow rate switch is connected to bypass the resistor.

6. The injection channel according to claim 1, wherein a resistor is coupled in parallel to the temperature sensor and the flow rate switch is connected in series to the resistor.

7. The injection channel according to claim 1, wherein the flow rate switch is actuated by an elastic membrane which is displaced by the influence of the fluid flow inside the injection channel.

8. The injection channel according to claim 1, wherein the flow rate switch comprises a REED-switch outside the injection channel being actuated by a movable magnet biased by an elastic member in the injection channel, the magnet being displaced by the influence of the fluid flow inside the injection channel.

9. The injection channel according to claim 1, wherein the flow rate switch comprises a REED-switch outside the injection channel and a magnet outside the injection channel at a side opposite to the REED-switch, the REED-switch being actuated by the influence of the movement of a movable ferromagnetic member biased by an elastic member in the injection channel which ferromagnetic member is displaced by the influence of the fluid flow inside the injection channel whereby the ferromagnetic member shields the REED-switch from the magnet in a first position and exposes the REED-switch to the magnet in a second position.

10. The injection channel according to claim 1, which can be connected to an injectate source at one side and to a blood vessel catheter at the other side.

11. The injection channel according to claim 1, wherein the flow rate switch and the temperature sensor are arranged at least partially in a separate removable housing.

12. An injection channel for a blood vessel catheter for injecting an injectate fluid into a blood vessel of a patient for carrying out thermodilution or dye-dilution measurements in order to determine hemodynamic parameters of the patient, the injection channel comprising:

a temperature sensor inside the injection channel for sensing the temperature of the injectate fluid passing through the injection channel;

a computer coupled to the temperature sensor for detecting changes of temperature readings as instants of begin and end of an injection process; and a pressure switch which is opened or closed if the pressure in the injection channel exceeds a threshold, wherein the pressure switch is electrically coupled to the output of the temperature sensor in such a manner that in case the pressure inside the injection channel is lower than the threshold, the readings of the temperature sensor are modified to indicate a temperature which deviates from the true temperature readings and in case the pressure inside the injection channel is exceeding the threshold, the readings of the temperature sensor are switched abruptly to the true readings.

13. The injection channel according to claim 12, wherein the pressure switch is an NO-switch and is coupled in a serial circuit with regard to the output of the temperature sensor.

14. The injection channel according to claim 12, wherein the pressure switch is an NC-switch and is coupled in a parallel circuit with regard to the output of the temperature sensor.

15. The injection channel according to claim 12, wherein a resistor is coupled in series to the temperature sensor and the pressure switch is connected to bypass the resistor.

16. The injection channel according to claim 12, wherein a resistor is coupled in parallel to the temperature sensor and the pressure switch is connected in series to the resistor.

17. The injection channel according to claim 12, wherein the pressure switch is actuated by an elastic membrane which is displaced by the influence of the pressure inside the injection channel.

18. The injection channel according to claim 12, wherein the pressure switch comprises a REED-switch outside the injection channel being actuated by a movable magnet biased by an elastic member in the injection channel, the magnet being displaced by the influence of the pressure inside the injection channel.

19. The injection channel according to claim 12, wherein the pressure switch comprises a REED-switch outside the injection channel and a magnet outside the injection channel at a side opposite to the REED-switch, the REED-switch being actuated by the influence of the movement of a movable ferromagnetic member biased by an elastic member in the injection channel which ferromagnetic member is displaced by the influence of the pressure inside the injection channel whereby the ferromagnetic member shields the REED-switch from the magnet in a first position and exposes the REED-switch to the magnet in a second position.

20. The injection channel according to claim 12, further comprising a throttle device inside the injection channel downstream of the pressure switch.

21. The injection channel according to claim 12, further comprising a check valve inside the injection channel that opens if a certain pressure is exceeded.

22. The injection channel according to claim 12, which can be connected to an injectate source at one side and to a blood vessel catheter at the other side.

23. The injection channel according to claim 12, wherein the pressure switch and the temperature sensor are arranged at least partially in a separate removable housing.

* * * * *